United States Patent [19]

Hawkins

[11] Patent Number: 4,487,068
[45] Date of Patent: Dec. 11, 1984

[54] METHOD AND APPARATUS FOR DETECTING ACOUSTIC EMISSIONS FROM METAL MATRIX WIRE

[75] Inventor: Gary F. Hawkins, Redondo Beach, Calif.

[73] Assignee: The United States of America as represented by the Secretary of the Air Force, Washington, D.C.

[21] Appl. No.: 502,771

[22] Filed: Jun. 9, 1983

[51] Int. Cl.³ .......................................... G01N 29/04
[52] U.S. Cl. ........................................ 73/587; 73/159
[58] Field of Search .................. 73/587, 801, 159, 160

[56] References Cited

U.S. PATENT DOCUMENTS

| | | | |
|---|---|---|---|
| 2,040,874 | 5/1936 | Pack | 73/801 |
| 2,795,136 | 6/1957 | Matt | 73/862.48 |
| 3,426,589 | 2/1969 | Brendel | 73/862.48 |
| 3,855,847 | 12/1974 | Leschek | 73/587 |

OTHER PUBLICATIONS

C. D. Bailey et al., "Acoustic Emission Monitors Damage Progression in Graphite Epoxy Composite Structure", *Materials Evaluation*, pp. 21–27, Aug. 1980.
Drouillard, Liptai and Tatro, "Industrial Use of Acoustic Emission for Nondestructive Testing," *Monitoring Structural Integrity by Acoustic Emission*, ASTM Special Technical Publication 571, 1975, pp. Contents, 122–149.
Williams, *Acoustic Emission*, Adam Hilger Ltd., 1980, pp. Contents, 69–70, 104–110.
Lenain, "General Principles of Acoustic Emission," *Materials Evaluation*, Oct. 1981, vol. 39, pp. 100–102.
Parry, "Acoustic Emission Inspection," *Material Evaluation*, Oct. 1981, vol. 39, pp. 1004–1005.
Sheriff, "New Horizons for Acoustic Emission," *Material Evaluation*, Oct. 1981, vol. 39, pp. 1018–1019.

*Primary Examiner*—Stephen A. Kreitman
*Attorney, Agent, or Firm*—Donald J. Singer; John R. Flanagan

[57] ABSTRACT

Apparatus for detecting acoustic emissions from metal matrix wire allows on-line measurement of the transverse strength of the wire as it is moving through its manufacturing process. A series of end and middle rollers guide the wire and form a bend in it. The location of the bend in the wire is maintained in contact with a liquid bath which, in turn, is contacted by the sensing surface of an acoustic transducer. Acoustic emissions from breaking of the fiber-matrix interface of the wire are transmitted by the bath and detected by the transducer.

6 Claims, 2 Drawing Figures

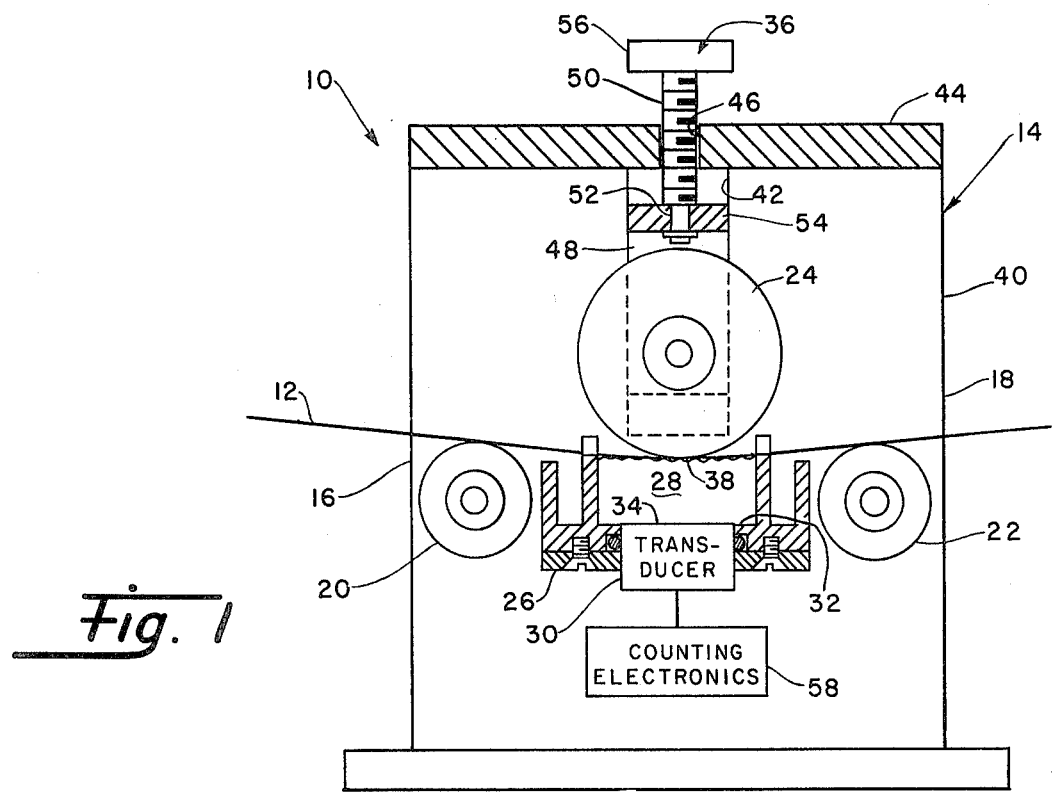
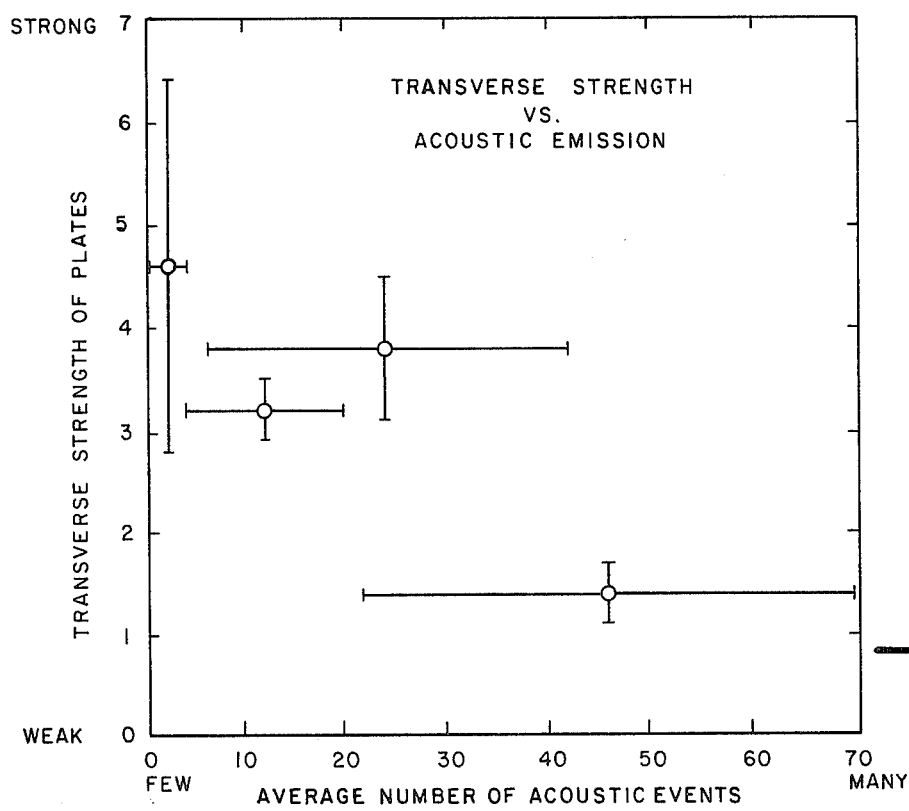

METHOD AND APPARATUS FOR DETECTING ACOUSTIC EMISSIONS FROM METAL MATRIX WIRE

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to nondestructive testing during manufacturing and, more particularly, is concerned with apparatus and method for detecting acoustic emissions from metal matrix wire to test its transverse strength as it is being manufactured.

2. Description of the Prior Art

Metal matrix wire such as a graphite-reinforced metal wire is manufactured by a conventional process involving liquid infiltration of fiber bundles. While this material has very good longitudinal properties, its transverse tensile strength may be poor due to a weak fiber-matrix interface. Therefore, it is common practice to test the transverse strength of this material.

However, heretofore, the only way to measure the transverse strength of the wire has been by destructively testing a plate made from the wires. This method has several disadvantages. It is time-consuming, does not provide a real-time measurement, and only tests samples of the wire.

Consequently, a need exists to devise a testing method less time-consuming than the present method and adapted to provide 100% testing of the wire in a real-time manner as the wire is being manufactured.

SUMMARY OF THE INVENTION

The present invention provides an apparatus and method for detecting acoustic emissions from metal matrix wire designed to satisfy the aforementioned needs. The invention allows on-line nondestructive testing of the wire and, thereby, real-time measurement of the transverse strength of the wire as it is being manufactured. Specifically, as the wire is moving through the manufacturing process, it is stressed and any acoustic emissions from breaking of its fiber-matrix interface are detected and counted. The number of acoustic emissions counted per a given length of wire correlates to the particular transverse tensile strength of the wire. The lengths of wire with the greatest number of acoustic emissions (or being the noisiest) have the weakest transverse strengths.

Accordingly, the present invention is directed to an apparatus and method for detecting acoustic emissions from a moving metal matrix wire for providing on-line, real-time testing of the transverse strength of a strand of the wire as it is being manufactured, which includes the operative steps of: (a) forming a bend in the strand of wire as it is moving; (b) maintaining the moving strand of wire at the location of its bend in contact with a liquid bath such that acoustic emissions given off by the wire due to formation of the bend therein will be transmitted by the liquid bath; and (c) contacting the liquid bath with an acoustic transducer for detecting the emissions given off by the wire and transmitted by the bath. The bend is formed in the strand of wire by means in the form of an upright support frame, a pair of end rollers disposed at entry and exit sides of the frame, a middle roller movably mounted to the frame between the end rollers for guiding the moving strand of wire between the end rollers on one side of the wire and the middle roller on the opposite side of the wire, and means for adjusting the middle roller relative to the end rollers and liquid bath to form the bend and maintain the strand of wire at the location of its bend in contact with the bath.

BRIEF DESCRIPTION OF THE DRAWINGS

FIG. 1 is a front elevational view in schematic form of the acoustic emissions detecting apparatus of the present invention.

FIG. 2 is a graph of the number of acoustic emissions detected from given lengths of different wires plotted against the transverse tensile strengths of plates made with those different wires.

DETAILED DESCRIPTION OF THE INVENTION

Before entering into a detailed description of the preferred embodiment of the apparatus for detecting acoustic emissions from metal matrix wire, it would first be of benefit to briefly discuss some general principles involved in acoustic emission testing.

Conventional Principles of Acoustic Emission Testing

Acoustic emission (AE) is defined as the transient elastic energy that is spontaneously released when materials undergo deformation, fracture, or both. It forms the basis of one of the few nondestructive testing (NDT) methods that provides a means of evaluating structural integrity by the detection of active flaws that may ultimately cause failure of the material or structure. Detection of AE represents actual detection of fracture events as they occur.

Consequently, in AE testing the defect or flaw in the material plays an active role in its own evaluation, rather than the passive role it usually plays during evaluation by other conventional NDT methods. Thus, AE is a dynamic test, limited to the detection of an active flaw during a change in the stress field around the flaw. It cannot detect static flaws. This is why the AE method of NDT must be carried out during tests or operations which stress the material or structure. Some conventional means of stressing the material or structure that are often used in AE testing are pressurization, tensile or compressive loading, and thermal stressing. It should be remembered, however, when selecting the level of stress to apply to the structure, that AE testing is nondestructive to acceptable structure, but may be destructive to defective ones.

Additional background information on AE and its application in NDT may be gained from an article by Jean-Claude Lenain, entitled "General Principles of Acoustic Emission," appearing in *Materials Evaluation*, October 1981, pages 1000-1002.

Preferred Embodiment of Present Invention

Turning now to the preferred embodiment of the present invention, FIG. 1 depicts in schematic fashion an apparatus, generally designated 10, for detecting acoustic emissions from a moving strand of wire 12, such as a metal matrix wire. By detecting acoustic emissions from the wire 12 while it is moving, the apparatus 10 may provide on-line, real-time testing of the transverse strength of the wire as it is being manufactured. In such manner, wires of weak transverse strength may be weeded out. Also, the apparatus may be used as a process control to alert the operator when something goes wrong with the wire manufacturing system.

As seen in FIG. 1, the acoustic emissions detecting apparatus 10 includes an upright support frame 14 having entry and exit sides 16, 18, a pair of end rollers 20, 22 stationarily mounted for rotation at the entry and exit sides 16, 18 of the frame 14, and a rotatable middle roller 24 movably mounted to the frame 14 between the end rollers 20, 22. The end rollers 20, 22 are disposed in spaced apart relationship and aligned with one another at a predetermined, generally horizontal level. The middle roller 24 is mounted in offset relationship above the level of the end rollers for guiding the moving strand of wire 12 between the end rollers 20, 22 located on the lower side of the wire 12 and the middle roller 24 located on the upper side of the wire 12.

The apparatus 10 further includes a receptacle 26 mounted on the frame 14 between the end rollers 20, 22 and below the middle roller 24, and containing a liquid bath 28, such as water, therein. Also, an acoustic transducer 30 is mounted to the bottom 32 of the receptacle 26 such that its sensing surface 34 is disposed in contact with the liquid bath 28 contained in the receptacle 26.

Finally, means, generally designated 36, for movably adjusting the middle roller 24 relative to the end rollers 20, 22 and in a generally vertical direction toward and away from the receptacle 26 is mounted on the frame 14. By manuplating the adjusting means 36, the middle roller 24 may be moved toward the receptacle such that a slight bend 38 is formed in the wire 12 as the latter moves past (around) the middle roller 24. Also, the adjusting means 36 will retain the middle roller 24 in a desired position in which the location of the bend 38 in the wire will be maintained in contact with the liquid bath 28, as seen in FIG. 1, as the strand of wire 12 moves past the middle roller 24.

More specifically, the support frame 14 includes an upright wall portion 40 having a generally vertical slot 42 defined in the upper half thereof and an overhead wall portion 44 extending outwardly in a generally horizontal direction from an upper end of the upright wall portion 40. The overhead wall portion 44 has a threaded hole 46 defined therein. The support frame 14 further includes a bracket 48 slidably mounted in the slot 42 in the upright wall portion 40. The bracket 48 stationarily mounts the middle roller 24 for rotation thereon and for movement therewith toward and away from the receptacle 26. The adjusting means 36 includes a shaft 50 threaded into the hole 46 in the overhead wall portion 44 of the frame 14 and rotatably connected at its lower end 52 to an outwardly projecting tab 54 on the upper end of the bracket 48. By rotating a knob 56 fixed on the upper end of the shaft 50, the bracket 48 may be slidably lowered or raised and, in turn, the middle roller 24 moves toward or away from the receptacle 26 and the strand of wire 12 being guided between the end rollers 20, 22 and the middle roller 24.

Through experimentation it has been determined that the transverse strength of the metal matrix wire is correlated with the structural integrity of the fiber-matrix interface of the wire 12. A strand of wire with a weak fiber-matrix interface will have low transverse strength. Underlying the present invention is a recognition that the number of acoustic emissions from the breaking or fracturing of the fiber-matrix interface when the wire is laterally stressed is correlated with the transverse strength of the wire. This relationship is illustrated in FIG. 2. It can be seen that the noisest wires have the weakest transverse strengths and vice versa.

In other words, by subjecting the wire to a bend 38 as it passes around middle roller 24, in the manner previously described, the side of the wire closest to the roller is placed in compression. If the fiber-matrix interface is weak enough, it breaks as the fibers of the wire buckle at the location of the bend 38. The sound of this interface cracking is transmitted through the liquid bath from the wire 12 to the transducer 30. The number of acoustic emissions per given length of wire may be counted by suitable conventional counting electronics 58 electrically connected to the transducer 30. Such electronics form no part of the present invention, so need not be disclosed in detail herein. Suitable components making up such electronics are described in the above-referenced article by Lenain.

In summary, the greater the number of acoustic emissions detected by the transducer 30 per given length of wire 12, the weaker the transverse strength of that length of the strand of wire. On the other hand, the fewer the number of emissions detected, the greater the transverse strength of the wire. The present invention allows this determination to be made on real-time basis during manufacturing as soon as the moving wire strand has left its fabricating station (not shown).

It is thought that the acoustic emission detecting apparatus and method of the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore being merely a preferred or exemplary embodiment thereof.

Having thus described the invention, what is claimed is:

1. Apparatus for detecting acoustic emissions from a moving metal matrix wire or the like for providing on-line, real-time testing of the transverse strength of a strand of said wire as it is being manufactured, comprising:
 (a) a receptacle containing a liquid bath therein;
 (b) an acoustic transducer mounted to said receptacle and having a sensing surface disposed in contact with said liquid bath; and
 (c) means for forming a bend in said strand of wire as the same is moving and for maintaining said moving strand of wire at the location of its bend in contact with said liquid bath such that acoustic emissions given off by said wire due to formation of said bend therein will be transmitted by said liquid bath and detected by said transducer.

2. Acoustic emissions detecting apparatus as recited in claim 1, wherein said means for forming said bend in said strand of wire includes:
 an upright support frame having entry and exit sides;
 a pair of end rollers disposed in spaced apart relationship, aligned with one another at a predetermined level, and stationarily mounted for rotation at said entry and exit sides of said frame;
 a middle roller movably mounted to said frame generally between said end rollers and adjacent said receptacle for guiding said moving strand of wire between said end rollers on one side of said wire and said middle roller on an opposite side of said wire;

means for movably adjusting said middle roller relative to said end rollers and receptacle to form said bend and maintain said strand of wire at the location of said bend in contact with said liquid bath.

3. Acoustic emissions detecting apparatus as recited in claim 2, wherein:

said end rollers are generally horizontally aligned at said predetermined level; and said middle roller is mounted in offset relationship above said level of said end rollers.

4. Acoustic emissions detecting apparatus as recited in claim 2, wherein:

said support frame includes an upright wall portion having a generally vertical slot defined therein and an overhead wall portion extending outwardly in a generally horizontal direction from an upper end of said upright wall portion and having a threaded hole defined therein.

5. Acoustic emission detecting apparatus as recited in claim 4, wherein:

said support frame further includes a bracket mounted in said slot in said upright wall portion which bracket, in turn, stationarily mounts said middle roller for rotation thereon and for movement therewith toward and away from said receptacle; and said adjusting means includes a shaft threaded into said hole in said overhead wall portion of said frame and connected to said bracket, and a knob on said shaft for rotating the same to vertically move said middle roller toward and away from said receptacle and said strand of wire being guided between said end rollers and said middle roller.

6. Method for detecting acoustic emissions from a moving metal matrix wire or the like for providing on-line, real-time testing of the transverse strength of a strand of said wire as it is being manufactured, comprising the steps of:

(a) forming a bend in said strand of wire as the same is moving;

(b) maintaining said moving strand of wire at the location of its bend in contact with a liquid bath such that acoustic emissions given off by said wire due to formation of said bend therein will be transmitted by said liquid bath; and (c) contacting said liquid bath with an acoustic transducer for detecting said emissions given off by said wire and transmitted by said bath.

* * * * *